(12) United States Patent
Türk et al.

(10) Patent No.: US 10,174,156 B2
(45) Date of Patent: *Jan. 8, 2019

(54) HYPERBRANCHED POLYESTER WITH A HYDROPHOBIC NUCLEUS FOR SOLUBILIZING POORLY SOLUBLE ACTIVE SUBSTANCES

(75) Inventors: Holger Türk, Mannheim (DE); Monika Haberecht, Ludwigshafen (DE); Hiroe Yamada, Saarbrücken (DE); Bernd Bruchmann, Freinsheim (DE); Daniel Schönfelder, Brussels (BE); Michael Ishaque, Mannheim (DE); Ulrike Troppmann, Schifferstadt (DE); Joachim Clauss, Darmstadt (DE); Chee Chin Liew, Bad Dürkheim (DE)

(73) Assignee: BASF SE, Ludwigshafen (DE)

( * ) Notice: Subject to any disclaimer, the term of this patent is extended or adjusted under 35 U.S.C. 154(b) by 177 days.

This patent is subject to a terminal disclaimer.

(21) Appl. No.: 13/515,857

(22) PCT Filed: Dec. 15, 2010

(86) PCT No.: PCT/EP2010/069680
§ 371 (c)(1),
(2), (4) Date: Aug. 8, 2012

(87) PCT Pub. No.: WO2011/073220
PCT Pub. Date: Jun. 23, 2011

(65) Prior Publication Data
US 2012/0309626 A1 Dec. 6, 2012

(30) Foreign Application Priority Data
Dec. 18, 2009 (EP) .................................... 09179828

(51) Int. Cl.
| C08G 63/12 | (2006.01) |
| A01N 25/02 | (2006.01) |
| A01N 25/30 | (2006.01) |
| A61K 47/34 | (2017.01) |

(52) U.S. Cl.
CPC ............. *C08G 63/12* (2013.01); *A01N 25/02* (2013.01); *A01N 25/30* (2013.01); *A61K 47/34* (2013.01)

(58) Field of Classification Search
CPC ................................ C08G 63/12; A61K 47/34
USPC ....................................................... 514/772.3
See application file for complete search history.

(56) References Cited

U.S. PATENT DOCUMENTS

| 3,697,428 A | 10/1972 | Meinhardt et al. |
| 5,872,149 A | 2/1999 | Dralle-Voss et al. |
| 2003/0118692 A1 | 6/2003 | Wang et al. |
| 2008/0312384 A1* | 12/2008 | Bruchmann ......... C08G 83/005 525/449 |
| 2009/0099319 A1 | 4/2009 | Stumbe et al. |

FOREIGN PATENT DOCUMENTS

| DE | 195 05 100 | 8/1996 | |
| WO | WO 2007068632 A1 * | 6/2007 | ........... C08G 83/005 |
| WO | WO 2007/125028 | 11/2007 | |
| WO | WO 2008/013107 | 1/2008 | |
| WO | WO 2008/059234 | 5/2008 | |

OTHER PUBLICATIONS

International Search Report, PCT/EP2010/069680, completed Feb. 9, 2011, 3pp.
International Preliminary Report on Patentability, PCT/EP2010/069680, dated Jul. 2011, 4pp.
Database WPI, Week 200830, Thomson Scientific, London, GB, AN 2008-E48995, XP002621383, WO 2008/013107, Jan. 31, 2008.

* cited by examiner

*Primary Examiner* — Gina C Justice
(74) *Attorney, Agent, or Firm* — Brinks Gilson & Lione

(57) ABSTRACT

The invention provides a composition comprising an active ingredient with a maximum solubility in water at 20° C. of 10 g/l, and a hyperbranched polyester based on a hydrophobic dicarboxylic acid and a trifunctional alcohol. The invention further relates to the hyperbranched polyester mentioned, to a process for preparation thereof and to the use thereof for solubilizing an active ingredient with a maximum solubility in water at 20° C. of 10 g/l in aqueous solutions.

4 Claims, No Drawings

HYPERBRANCHED POLYESTER WITH A HYDROPHOBIC NUCLEUS FOR SOLUBILIZING POORLY SOLUBLE ACTIVE SUBSTANCES

This application is a National Stage application of International Application No. PCT/EP2010/069680 filed Dec. 15, 2010, the entire contents of which is hereby incorporated herein by reference. This application also claims priority under 35 U.S.C. § 119 to EP Patent Application No. 09179828.0, filed Dec. 18, 2009, the entire contents of which is hereby incorporated herein by reference.

The invention provides a composition comprising an active ingredient with a maximum solubility in water at 20° C. of 10 g/l, and a hyperbranched polyester based on a hydrophobic dicarboxylic acid and a trifunctional alcohol. The invention further relates to the hyperbranched polyester mentioned, to a process for preparation thereof and to the use thereof for solubilizing an active ingredient with a maximum solubility in water at 20° C. of 10 g/l in aqueous solutions. Combinations of preferred features with other preferred features are encompassed by the present invention.

In many cases it is necessary to solubilize hydrophobic active ingredients in water without chemically modifying the relevant active ingredient per se. For this purpose it is possible for example to prepare an emulsion in which the relevant active ingredient is in the oil phase of the emulsion. However, with many active pharmaceutical ingredients or especially crop protection compositions, especially in the case of those which are to be transported with a body fluid or in a plant's sap, an approach of this kind is not possible. Under the action of high shearing forces it is, possible for emulsions to break. Moreover, sterilizing while retaining the emulsion is in many cases not a possibility.

Compositions comprising an active ingredient and a hyperbranched polyester are common knowledge: WO 2007/125028 discloses a process for solubilizing hydrophobic active ingredients in an aqueous medium, wherein a hyperbranched polyester which has optionally been reacted with a polyalkylene oxide unit which bears an isocyanate group is used. To prepare the polyester, a wide variety of different dicarboxylic acids are described, such as sebacic acid, and a wide variety of different trifunctional alcohols, such as glycerol, trimethylolpropane, pentaerythritol and alkoxylated derivatives thereof.

Hyperbranched polyesters are common knowledge: WO 2009/047210 discloses hyperbranched polyesters comprising dicarboxylic acid units and trifunctional alcohols, the dicarboxylic acid units described being succinic acid units substituted by $C_3$-$C_{40}$ alkyl radicals or alkenyl radicals. A wide variety of different trifunctional alcohols are mentioned, such as glycerol, trimethylolpropane, pentaerythritol and alkoxylated derivatives thereof. WO 2007/068632 discloses hyperbranched polyesters obtainable by reacting dicarboxylic acids having polyisobutene groups and trifunctional alcohols such as glycerol, trimethylolpropane, pentaerythritol and the alkoxylated derivatives thereof.

A disadvantage of the known hyperbranched polyesters is that they can solubilize only small amounts of sparingly soluble active ingredients since they do not usually possess a markedly amphiphilic structure. Moreover, the polyesters are often themselves not water-soluble or not water-dispersible, such that they are unsuitable for solubilization in aqueous media. Even a neutralization of the carboxylic acid groups present generally cannot achieve water solubility, since the acid number is usually very low, for example less than 50 or even less than 20 mg KOH per g of polymer.

The polyesters listed as preferred structures in WO 2007/125028 are additionally hydrolytically unstable owing to the relatively polar, short-chain dicarboxylic acid components (e.g. succinic acid, adipic acid), and they are therefore not very suitable for producing storage-stable aqueous active ingredient formulations, especially in the agrochemical sector.

It was an object of the present invention to find an alternative hyperbranched polyester which is suitable for solubilizing sparingly soluble active ingredients, in particular in an aqueous medium. It was a further object to find a polyester which can solubilize maximum amounts of active ingredient, especially active agrochemical ingredient, and which should have maximum stability, especially hydrolytic stability. In addition, the polyester should itself be water-soluble or water-dispersible, either by virtue of functionalization by means of a polyalkylene oxide group and/or of a functional $C_1$-$C_{24}$ end group comprising one acid group or two alcohol groups, and/or by virtue of the existence of numerous, optionally (partly) neutralizable carboxylic acid groups. Finally, it was also an object of the invention to find a hyperbranched polyester which is preparable readily from commercially available chemicals and in an industrially reliable manner.

The object was achieved by a composition comprising an active ingredient with a maximum solubility in water at 20° C. of 10 g/l, and a hyperbranched polyester based on a hydrophobic dicarboxylic acid and a trifunctional alcohol, wherein the hydrophobic dicarboxylic acid is an aliphatic $C_{10}$-$C_{32}$ dicarboxylic acid, a dicarboxylic acid having a polyisobutylene group and/or a succinic acid unit having a $C_3$-$C_{40}$ group, and the trifunctional alcohol is glycerol, trimethylolethane, trimethylolpropane, bis(trimethylolpropane), pentaerythritol, or an alkoxylated derivative thereof.

In a preferred embodiment, the hydrophobic dicarboxylic acid is an aliphatic $C_{10}$-$C_{32}$ dicarboxylic acid. In a further preferred embodiment, the hydrophobic dicarboxylic acid is a dicarboxylic acid having a polyisobutylene group. In a further preferred embodiment, the hydrophobic dicarboxylic acid is a succinic acid unit having a $C_3$-$C_{40}$ group. In a further preferred embodiment, the hydrophobic dicarboxylic acid is a dicarboxylic acid having a polyisobutylene group and/or a succinic acid unit having a $C_3$-$C_{40}$ group.

The maximum solubility of the active ingredient in water at 20° C. is 10 g/l, preferably 2 g/l, more preferably 0.5 g/l and especially 0.1 g/l. The composition may comprise one or more different active ingredients. Examples of active ingredients are active agrochemical ingredients, active cosmetic ingredients, active pharmaceutical ingredients or food supplements (such as vitamins or carotenoids). Preferred active ingredients are active agrochemical ingredients.

Examples of active cosmetic ingredients are cosmetic oils, flavorings and aromas, vitamins or UV absorbers. Cosmetic oils include groundnut oil, jojoba oil, coconut oil, almond oil, olive oil, palm oil, castor oil, soybean oil, wheatgerm oil, or essential oils such as mountain pine oil, lavender oil, rosemary oil, spruce needle oil, pine needle oil, eucalyptus oil, peppermint oil, sage oil, bergamot oil, terpentine oil, melissa oil, juniper oil, lemon oil, anise oil, cardamom oil, camphor oil, etc., or mixtures thereof. UV absorbers include 2-hydroxy-4-methoxybenzophenone, 2,2', 4,4'-tetrahydroxybenzophenone, 2,2'-dihydroxy-4,4'-dimethoxybenzophenone, 2,4-dihydroxybenzophenone, 2'-ethylhexyl 2-cyano-3,3-diphenylacrylate, 2,4,6-trianilino-p-(carbo-2'-ethylhexyl-1'-oxy)-1,3,5-triazine, 3-(4-methoxybenzylidene)camphor, 2-ethylhexyl N,N-dimethyl-4-aminobenzoate, 3,3,5-trimethylcyclohexyl salicylate, 4-isopropyldibenzoylmethane, 2-ethylhexyl p-methoxycinnamate and 2-isoamyl p-methoxycinnamate, and mixtures thereof.

Examples of flavorings and aromas are as described in WO 01/49817, or in "Flavors and Fragrances", Ullmann's Encyclopedia of Industrial Chemistry, Wiley-VCH, 2002, to which explicit reference is made.

Examples of vitamins are vitamins, provitamins and vitamin precursors from groups A, C, E and F, especially 3,4-didehydroretinol, beta-carotene (provitamin of vitamin A), ascorbic acid (vitamin C), and the palmitic esters, glucosides or phosphates of ascorbic acid, tocopherols, especially alpha-tocopherol and esters thereof, for example the acetate, the nicotinate, the phosphate and the succinate; and additionally vitamin F, which is understood to mean essential fatty acids, particularly linolic acid, linolenic acid and arachidonic acid.

Examples of active pharmaceutical ingredients include: benzodiazepines, antihypertensives, vitamins, cytostatics, especially taxol, anesthetics, neuroleptics, antidepressives, antiviral agents, for example anti-HIV agents, antibiotics, antimycotics, antidementia drugs, fungicides, chemotherapeutics, urologics, platelet aggregation inhibitors, sulfonamides, spasmolytics, hormones, immunoglobulins, sera, thyroid therapeutics, psychoactive drugs, Parkinson's drugs and other antihyperkinetics, ophthalmics, neuropathy preparations, calcium metabolism regulators, muscle relaxants, lipid-lowering drugs, hepatotherapeutics, coronary drugs, cardiac drugs, immunotherapeutics, regulatory peptides and inhibitors thereof, hypnotics, sedatives, gynecologicals, gout remedies, fibrinolytics, enzyme preparations and transport proteins, enzyme inhibitors, emetics, blood flow stimulators, diuretics, diagnostic agents, corticoids, cholinergics, biliary therapeutics, antiasthmatics, bronchodilators, beta receptor blockers, calcium antagonists, ACE inhibitors, arteriosclerosis drugs, antiinflammatories, anticoagulants, antihypotensives, antihypoglycaemics, antihypertensives, antifibrinolytics, antiepileptics, antiemetics, antidotes, antidiabetics, antiarrhythmics, antianaemics, antiallergics, anthelmintics, analgesics, analeptics, aldosterone antagonists, slimming agents.

The term "active agrochemical ingredients" (also referred to hereinafter as pesticides) refers to at least one active ingredient selected from the group of fungicides, insecticides, nematicides, herbicides, safeners and/or growth regulators. Preferred pesticides are fungicides, insecticides and herbicides, especially insecticides. Mixtures of pesticides from two or more of the abovementioned classes can also be used. The person skilled in the art is familiar with such pesticides, which can be found, for example, in Pesticide Manual, 14th Ed. (2006), The British Crop Protection Council, London. Suitable insecticides are insecticides from the class of carbamates, organophosphates, organochlorine insecticides, phenylpyrazoles, pyrethroids, neonicotinoids, spinosins, avermectins, milbemycins, juvenile hormone analogs, alkyl halides, organotin compounds, nereistoxin analogs, benzoylureas, diacylhydrazines, METI acaricides, and insecticides such as chloropicrin, pymetrozine, flonicamid, clofentezine, hexythiazox, etoxazole, diafenthiuron, propargite, tetradifon, chlorfenapyr, DNOC, buprofezin, cyromazine, amitraz, hydramethylnon, acequinocyl, fluacrypyrim, rotenone, or derivatives thereof. Suitable fungicides are fungicides of the classes dinitroanilines, allylamines, anilinopyrimidines, antibiotics, aromatic hydrocarbons, benzenesulfonamides, benzimidazoles, benzisothiazoles, benzophenones, benzothiadiazoles, benzotriazines, benzylcarbamates, carbamates, carboxamides, carboxylic acid amides, chloronitriles, cyanoacetamide oximes, cyanoimidazoles, cyclopropanecarboxamides, dicarboximides, dihydrodioxazines, dinitrophenylcrotonates, dithiocarbamates, dithiolanes, ethylphosphonates, ethylaminothiazolecarboxamides, guanidines, hydroxy-(2-amino) pyrimidines, hydroxyanilides, imidazoles, imidazolinones, inorganic compounds, isobenzofuranones, methoxyacrylates, methoxycarbamates, morpholines, N-phenylcarbamates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides of the classes of acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ethers, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, pyridinecarboxylic acids, pyridinecarboxamides, pyrimidinediones, pyrimidinyl(thio)benzoates, quinolinecarboxylic acids, semicarbazones, sulfonylaminocarbonyltriazolinones, sulfonylureas, tetrazolinones, thiadiazoles, thiocarbamates, triazines, triazinones, triazoles, triazolinones, triazolinones, triazolocarboxamides, triazolopyrimidines, triketones, uracils, ureas.

In one embodiment, the pesticide comprises an insecticide; the pesticide more preferably consists of at least one insecticide. Preferred insecticides are fipronil, allethrin, alpha-cypermethrin, beta-cyfluthrin, bifenthrin, bioallethrin, 4-chloro-2-(2-chloro-2-methylpropyl)-5-[(6-iodo-3-pyridinyl)methoxy]-3(2H)pyridazinone (CAS RN: 120955-77-3), chlorfenapyr, chlorpyrifos, cyfluthrin, cyhalothrin, cypermethrin, deltamethrin, etofenprox, fenoxycarb, flufenoxuron, hydramethylnon, metaflumizone, permethrin, pyriproxifen, silafluofen, tebufenozide and tralomethrin. Particularly preferred insecticides are fipronil, alpha-cypermethrin, bifenthrin, chlorfenapyr, cyfluthrin, cypermethrin, deltamethrin, etofenprox, hydramethylnon, metaflumizone, permethrin. Very particularly preferred insecticides are fipronil, alpha-cypermethrin, deltamethrin, chlorfenapyr, hydramethylnon and metaflumizone. An especially preferred insecticide is fipronil. In a further embodiment, the pesticide comprises a fungicide; the pesticide preferably consists of at least one fungicide. Preferred fungicides are pyraclostrobin, metconazol and epoxiconazol. In a further embodiment, the pesticide comprises a herbicide; the pesticide preferably consists of at least one herbicide. In a further embodiment, the pesticide comprises a growth regulator; the pesticide preferably consists of at least one growth regulator.

The inventive composition comprises typically 0.1 to 70% by weight of active ingredient, preferably 1 to 60% by weight, especially 3 to 50% by weight, based on the composition. The weight ratio of the hyperbranched polyester to the active ingredient is usually in the range from 1:2 to 25:1.

Dendrimeric and hyperbranched polymers are terms for polymers which are notable for a highly branched structure and a high functionality. However, there are nevertheless significant differences in structure between dendrimers and hyperbranched polymers. Dendrimers are molecularly homogeneous macromolecules with a highly symmetric structure. Dendrimers can, proceeding from a central molecule, be prepared by controlled stepwise linkage of in each case two or more di- or polyfunctional monomers to each already bonded monomer. Each linkage step multiplies the number of monomer end groups (and hence of linkages) by the factor of 2 or higher, and monodisperse polymers which are built up generation by generation and have treelike structures, ideally spherical, whose branches each comprise exactly the same number of monomer units, are obtained. Owing to the branched structure, the polymer properties are advantageous: for example, a surprisingly low viscosity and a high reactivity are observed owing to the high number of functional groups on the sphere surface. However, the preparation of the monodisperse dendrimers is complicated by the need to introduce protecting groups and remove them again in each linkage step, and by the requirement for intensive purifying operations before the start of each new growth stage, which is why dendrimers are typically prepared only on the laboratory scale.

In contrast, hyperbranched polymers are both molecularly and structurally inhomogeneous, i.e. the molecules of the polymer have a distribution both with regard to the molecular weight and with regard to the structure of the molecules. They are obtained by being built up in a non-generational manner. It is therefore also not necessary to isolate and to purify intermediates. Hyperbranched polymers can be obtained by simple mixing of the components required to form them and the reaction thereof in a so-called one-pot reaction. Hyperbranched polymers may have dendrimeric substructures. In addition, though, they also have linear polymer chains and inhomogeneous polymer branches.

Especially suitable for the synthesis of hyperbranched polymers are so-called $AB_x$ monomers. These have two different functional groups A and B in one molecule, which can react with one another in an intermolecular manner to form a bond. The functional A group is present only once per molecule and the functional B group twice or more than twice. The reaction of said $AB_x$ monomers with one another forms uncrosslinked polymers with a high number of branching sites. The polymers have almost exclusively B groups at the chain ends.

Moreover, hyperbranched polymers can be prepared via the $A_x+B_y$ synthesis route. In this case, $A_x$ and $B_y$ represent two different monomers with the functional groups A and B, and the indices x and y the number of functional groups per monomer. In the $A_x+B_y$ synthesis, illustrated here by the example of an $A_2+B_3$ synthesis, a difunctional monomer $A_2$ is reacted with a trifunctional monomer $B_3$. This initially forms a 1:1 adduct of A and B with an average of one functional A group and two functional B groups, which can then likewise react to give a hyperbranched polymer. The hyperbranched polymers thus obtained also have predominantly B groups as end groups.

The nondendrimeric hyperbranched polymers used in accordance with the invention differ from dendrimers significantly in the degree of branching. The degree of branching DB of the polymers in question is defined as DB=100*(T+Z)/(T+Z+L), where T is the mean number of terminally bound monomer units, Z is the mean number of monomer units forming branches and L is the mean number of linearly bound monomer units in the macromolecules of the particular polymers. For the definition of the "Degree of Branching", see also H. Frey et al., Acta Polym. 1997, 48, 30. In the context of the invention, the feature "hyperbranched" in connection with the polymers means that the degree of branching DB is from 10 to 95%, preferably 25 to 90% and more preferably from 30 to 80%. A dendrimer, in contrast, has the maximum possible number of branching sites, which can be achieved only by a highly symmetric structure. In connection with the present invention, the polymers are "dendrimers", in contrast, when their degree of branching DB=99 to 100%.

In a known manner, the polyesters have ester linkages. The polymers comprise, as structural units, in each case at least one hydrophobic dicarboxylic acid unit and at least one trifunctional alcohol. They may additionally comprise further structural units. The hyperbranched polyester is usually soluble or dispersible in water, which means that it is possible to prepare a clear (i.e. without particles discernible to the naked eye) aqueous solution or dispersion.

A suitable hydrophobic dicarboxylic acid is an aliphatic $C_{10}$-$C_{32}$ dicarboxylic acid. Preference is given to sebacic acid, α, ω-undecanedicarboxylic acid, α, ω-dodecanedicarboxylic acid, tridecanedicarboxylic acid (brassylic acid), especially sebacic acid.

Another suitable hydrophobic dicarboxylic acid is a dicarboxylic acid having a polyisobutylene group (also referred to hereinafter as "PIB diacid"). In this connection, a "dicarboxylic acid having a polyisobutylene group" has at least two dicarboxylic acid groups, at least two dicarboxylic ester groups or at least one dicarboxylic anhydride group (it preferably has one dicarboxylic anhydride group). Such PIB diacids are obtainable by reacting polyisobutylene with an enophile. In a preferred embodiment, the products are 1:1 (mol/mol) reaction products of an ene reaction of a polyisobutylene and of the enophile. The PIB diacid is prepared by the processes known to those skilled in the art and preferably as described in German laid-open specifications DE-A 195 19 042, preferably from page 2 line 39 to page 4 line 2 and more preferably from page 3 line 35 to 58, and DE-A 43 19 671, preferably from page 2 line 30 to line 68, and DE-A 43 19 672, preferably from page 2 line 44 to page 3 line 19, described processes for reacting polyisobutylenes with enophiles. The polyisobutylenes are preferably those which have to an extent of at least 60 mol % end groups formed from vinyl isomer and/or vinylidene isomer.

Suitable enophiles are fumaryl chloride, fumaric acid, itaconic acid, itaconyl chloride, maleyl chloride, maleic anhydride and/or maleic acid, preferably maleic anhydride or maleyl chloride, more preferably maleic anhydride.

The number-average molecular weight $M_n$, of the PIB acid is preferably at least 100 g/mol, more preferably at least 200 g/mol. In general, the number-average molar mass $M_n$ is up to 5000, more preferably up to 2000 g/mol. In a particularly preferred embodiment, the PIB acids have a number-average molecular weight $M_n$ of 1000+/−500 g/mol.

The PIB diacid preferably has a structure of the general formula (Ia), (Ib) or (Ic), in which PIB may be a polyisobutylenyl group which is obtained by any polymerization and has a number-average molecular weight $M_n$ of 100 to 100 000 daltons. Preference is given to formula (Ia), i.e. PIB-succinic anhydride.

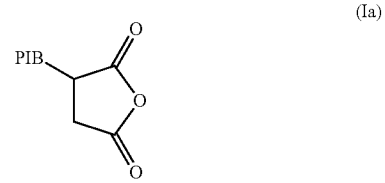

(Ia)

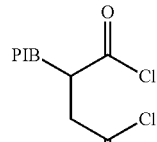

(Ib)

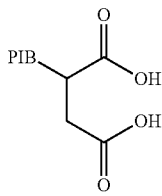

(Ic)

The number-average molecular weight $M_n$, of the thus obtainable and preferred succinic anhydride derivative substituted by a polyisobutylenyl group, known as "PIBSA", can be characterized by means of the hydrolysis number according to DIN 53401 in the unit mg KOH/g of substance. The synthesis of PIBSA is known in the literature as the ene reaction between maleic anhydride and polyisobutenes (see, for example, DE-A 43 19 672, EP-A 156 310).

During the ene reaction, a new α-olefin group is obtained at the chain end and is in turn again reactive. It is known to those skilled in the art that a reaction with further maleic anhydride affords a product which can thus bear two succinic anhydride groups per reactive chain end of the polyisobutene. This means that a polyisobutene from $BF_3$ catalysis, depending on the performance of the ene reaction, may bear one or even two succinic anhydride groups per chain. Consequently, polyisobutenes from living cationic polymerization in the reaction with maleic anhydride may likewise be mono- or disubstituted per reactive chain end. Thus, polyisobutenes are possible not just with one, but also with two and more succinic anhydride groups per molecule.

Since the reaction with maleic anhydride forms a new double bond which can likewise react with maleic anhydride, the succinic anhydrides which are substituted by a polyisobutylene group and are thus obtainable generally have a ratio of 0.9 to 1.5, preferably of 0.9 to 1.1, succinic anhydride groups per polyisobutylene chain. More preferably, each polyisobutylene chain bears only one succinic anhydride group.

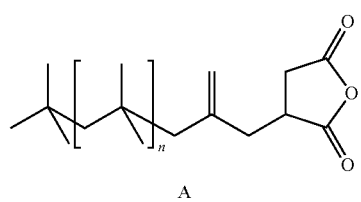

A

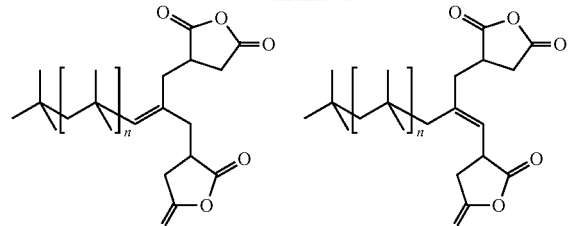

B

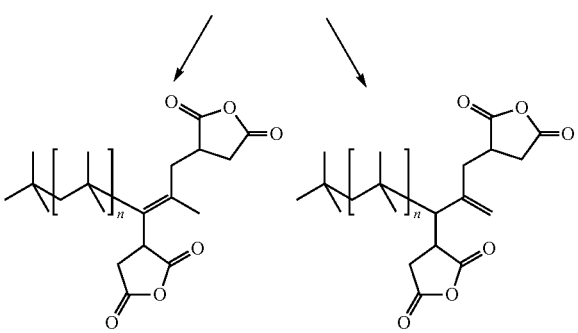

Shown above is an exemplary illustration of the product isomers of the single ene reaction and double ene reaction of an ideal polyisobutene having a single reactive chain end. Isomers are shown with one (alpha-olefin PIBSA, "A"; beta-olefin PIBSA, "B") or two succinic anhydride group(s) on one chain end. Analogously, however, PIBSAs having two and more chain ends are accordingly possible with one or two succinic anhydride radicals per chain end in the different isomeric variants of mono- and disubstitution. The number of possible isomers thus rises sharply with the number of chain ends. The person skilled in the art knows that, depending on the reaction, different substitution patterns can be realized with different isomer contents of the PIBSA.

The degree of functionalization, i.e. the fraction of the α- or β-olefinic end groups reacted with the enophile in the polyisobutene, of the polyisobutylene derivatives modified with terminal succinic anhydride groups is in total at least 65 mol %, preferably at least 75 mol % and most preferably at least 85 mol %. In the case of the polymers with only one reactive chain end, the degree of functionalization relates only to this one functional group with the two possible isomers α- and β-olefin PIBSA. In the disubstituted and polysubstituted PIBSA derivatives, the data for the degrees of functionalization are based on the total number of all functional groups within one molecule chain. Depending on whether mono- or disubstitution is present at one chain end, isomers depicted above are present in varying fractions.

The nonfunctionalized chain ends may either be those which have no reactive group at all (i.e. no α- or β-olefin radical) or those which do have a reactive group (α- or β-olefin radical) but which have not been reacted with maleic anhydride in the course of the ene reaction. In summary, the degree of functionalization thus relates only to the number of all functional groups present in one polymer chain, but not their possible isomers.

In addition, the copolymerization of maleic anhydride and polyisobutenes is also described, for example in WO 90/03359, EP B1 644 208, EP B1 744 413. The products thus prepared are known under the name polyPIBSA. In comparison to the ene reaction, however, copolymerization plays a comparatively minor role. This copolymerization of maleic anhydride and polyisobutenes, using free-radical initiators, forms alternating copolymers with comb structure. No homopolymers are known either of maleic anhydride or of polyisobutenes with olefinic end groups. It can thus be assumed that polyPIBSAs have a strictly alternating structure. A degree of functionalization as for the PIBSAs with terminal succinic anhydride units from the ene reaction cannot be specified. The structure of polyPIBSAs is depicted below.

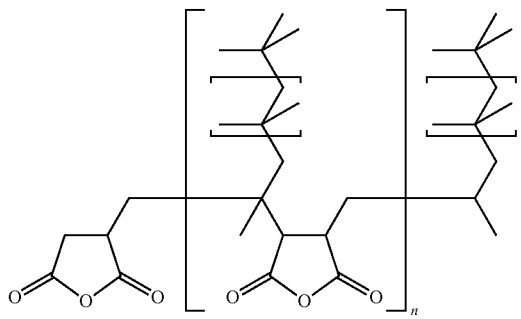

Suitable hydrophobic dicarboxylic acids are also succinic acid units having $C_3$-$C_{40}$ groups, preferably substituted succinic acid units of the formula (II)

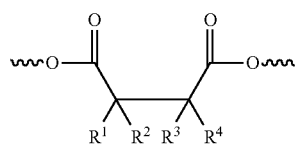

where $R^1$, $R^2$, $R^3$ and $R^4$ are each independently H, a $C_3$ to $C_{40}$-alkyl radical or a $C_3$ to $C_{40}$-alkenyl radical, with the proviso that at least one of the $R^1$, $R^2$, $R^3$ and $R^4$ radicals is not H. The radicals are preferably alkenyl radicals. Preferably two or three of the $R^1$, $R^2$, $R^3$ or $R^4$ radicals are H, and more preferably three of the radicals are H, i.e. the succinic acid unit has only one alkyl or alklenyl group. The one substituent may be in the $R^1$ or $R^3$ position.

The alkyl radicals may be linear or branched. They are preferably $C_4$ to $C_{30}$ radicals, more preferably $C_6$ to $C_{28}$ radicals, even more preferably $C_8$ to $C_{26}$ radicals and, for example, $C_{10}$ to $C_{20}$ radicals. The alkyl chains are more preferably linear. For example, they may be butyl, pentyl, hexyl, heptyl, octyl, decyl, dodecyl, tetradecyl, hexadecyl, octadecyl or isooctadecyl radicals, preferably decyl, dodecyl, tetradecyl, hexadecyl, octadecyl or isooctadecyl radicals. If the radicals are branched, preferably not more than one branch per 3 carbon atoms of the radical should be present, more preferably not more than one branch per 4 carbon atoms of the radical.

Alkenyl radicals have one or else more than one double bond. They are preferably alkenyl radicals with one double bond. The alkenyl radicals may be linear or branched. If the radicals are branched, preferably not more than one branch should be present per 3 carbon atoms of the radical, preferably not more than one branch per 4 carbon atoms of the radicals. They are preferably $C_4$ to $C_{30}$ radicals, more preferably $C_6$ to $C_{28}$ radicals, even more preferably $C_{10}$ to $C_{26}$ radicals and, for example, $C_{10}$ to $C_{20}$ radicals. The alkenyl radicals may preferably be n- or isohexenyl, n- or isoheptenyl, n- or isooctenyl, n- or isooctadienyl, n- or isononenyl, n- or isodecenyl, n- or isododecenyl, n- or isotetradecenyl, n- or isohexadecenyl, n- or isooctadecenyl or tetrapropenyl radicals. The alkenyl radicals are more preferably n- or isooctenyl, n- or isododecenyl, n- or isotetradecenyl, n- or isohexadecenyl, n- or isooctadecenyl or tetrapropenyl radicals.

To synthesize the hyperbranched polyesters, it is possible to use succinic acid substituted in the manner described. The succinic acid may preferably be used, however, in the form of activated derivatives, especially in the form of halides, esters or anhydrides. Derivatives are especially the relevant anhydrides in monomeric or else polymeric form, mono- or dialkyl esters, preferably mono- or di-$C_1$-$C_4$-alkyl esters, more preferably mono- or dimethyl esters or the corresponding mono- or diethyl esters, and also mono- and divinyl esters and mixed esters, preferably mixed esters with different $C_1$-$C_4$-alkyl components, more preferably mixed methyl ethyl esters.

Particular preference is given to using succinic anhydrides as the starting material. In addition to the high reactivity of the anhydrides, the use of the anhydrides has the advantage that alkenylsuccinic anhydrides can be prepared in a particularly simple and inexpensive manner by reacting maleic anhydrides with olefins which have a hydrogen atom in the allyl position (the so-called ene reaction). Reaction of linear α-olefins can provide alkenylsuccinic anhydrides with n-alkenyl radicals; isomerized olefins with nonterminal double bonds give rise to succinic anhydrides substituted by isoalkenyl radicals. The olefins used may also be reactive oligo- or polyolefins, though reactive polyisobutenes are preferably not used. The preparation of alkenylsuccinic anhydrides (also known as ASA) by means of the ene reaction is described in detail, for example, in WO 97/23474 or DE 195 19 042 and the literature cited therein.

Succinic anhydrides substituted by alkenyl groups which are used with preference are n- or isohexenylsuccinic anhydride, n- or isoheptenylsuccinic anhydride, n- or isooctenylsuccinic anhydride, n- or isooctadienylsuccinic anhydride, n- or isononenylsuccinic anhydride, n- or isodecenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride, 2-dodecenyl-3-tetradecenylsuccinic anhydride. It will be appreciated that it is also possible to use mixtures of different substituted anhydrides.

Particularly preferred products are n- or isooctenylsuccinic anhydride, n- or isododecenylsuccinic anhydride (DDSA), n- or isotetradecenylsuccinic anhydride, n- or isohexadecenylsuccinic anhydride, n- or isooctadecenylsuccinic anhydride, tetrapropenylsuccinic anhydride or mixtures of the products mentioned. Very particular preference is given to n- or isohexadecenylsuccinic anhydride, n- or isooctadecenylsuccinic anhydride, or mixtures thereof.

The alkenylsuccinic acids or derivatives or mixtures thereof can also be used in a mixture with alkylsuccinic acids or derivatives thereof.

To prepare the hyperbranched polyesters, at least one hydrophobic dicarboxylic acid is reacted with at least one trifunctional alcohol, the ratio of the reactive groups in the reaction mixture being selected such that a molar ratio of OH groups to carboxyl groups or derivatives thereof of 5:1 to 1:5, preferably of 4:1 to 1:4, more preferably of 3:1 to 1:3 and most preferably of 2:1 to 1:2 is established. When mixtures of hydrophobic aliphatic $C_{10}$-$C_{32}$ dicarboxylic acids and/or dicarboxylic acids having polyisobutylene groups and/or succinic acid units having a $C_3$-$C_{40}$ group are used, the stoichiometry of OH groups to carboxyl groups is usually maintained as described above.

Trifunctional alcohols are understood to mean alcohols with at least three alcohol groups. Suitable trifunctional alcohols are glycerol, trimethylolethane, trimethylolpropane, bis(trimethylolpropane), pentaerythritol, or an alkoxylated, preferably ethoxylated or propoxylated) derivative thereof. It will be appreciated that it is also possible to use mixtures of a plurality of different trifunctional alcohols. Preferred trifunctional alcohols are glycerol, trimethylolpropane and pentaerythritol. Very particular preference is given to glycerol and trimethylolpropane.

Alkoxylated derivatives of glycerol, trimethylolethane, trimethylolpropane, bis(trimethylolpropane), pentaerythritol can be obtained in a manner known in principle by alkoxylating the alcohols with alkylene oxide, such as ethylene oxide, propylene oxide, butylene oxide, and/or pentylene oxide. The mixed alkoxylated polyetherols may be copolymers in which, for example, different alkylene oxide units are distributed randomly in the chain, or they may be block copolymers.

The alkoxylated derivative of glycerol, trimethylolethane, trimethylolpropane; bis(trimethylolpropane) or pentaerythritol is preferably alkoxylated with 1.1 to 20 alkylene oxide units, preferably ethylene oxide and/or propylene oxide units. The alkoxylated derivative of glycerol, trimethylolpropane or pentaerythritol is most preferably alkoxylated with 1.1 to 20 propylene oxide units.

In addition to the components mentioned, it is optionally also possible to use further components to synthesize the hyperbranched polymers used in accordance with the invention. Such components can be used to influence the properties of the polymers and adjust them optimally for the desired purpose.

For instance, it is possible to use further di- or polyfunctional carboxylic acids. Examples of further carboxylic acids comprise malonic acid, succinic acid, glutaric acid, adipic acid, 1,2-, 1,3- or 1,4-cyclohexanedicarboxylic acid (hexahydrophthalic acids), phthalic acid, isophthalic acid, terephthalic acid or derivatives thereof, especially the anhydrides or esters thereof. The amount of such further carboxylic acids should, however, generally not exceed 50 mol % based on the amount of all carboxylic acids used (i.e. sum of hydrophobic dicarboxylic acids and further di- or polyfunctional carboxylic acids) together.

In addition, as well as the trifunctional alcohols, it is also possible to use difunctional aliphatic, cycloaliphatic, araliphatic or aromatic diols. The suitable selection of dihydric alcohols can influence the properties of the polyesters. Examples of suitable diols are ethylene glycol, 1,2-propanediol, 1,3-propanediol, 1,4-butanediol, 1,5-pentanediol, 1,6-hexanediol, 1,8-octanediol, 1,2-, 1,3- and 1,4-cyclohexanediol, 1,3- and 1,4-bis(hydroxymethyl)cyclohexane, and also diethylene glycol, triethylene glycol, dipropylene glycol, tripropylene glycol, polyethylene glycols $HO(CH_2CH_2O)_n$—H or polypropylene glycols $HO(CH[CH_3]CH_2O)_n$—H, where n is an integer and n is 4, polyethylene-polypropylene glycols, where the sequence of the ethylene oxide or propylene oxide units may be blockwise or random, or polytetramethylene glycols, preferably up to a molar mass of 5000 g/mol. The dihydric alcohols may optionally also comprise further functionalities, for example carbonyl, carboxyl, alkoxycarbonyl or sulfonyl functions, for example dimethylolpropionic acid or dimethylolbutyric acid, and the $C_1$-$C_4$-alkyl esters thereof, glyceryl monostearate or glyceryl monooleate. The amount of such further dihydric alcohols should, however, generally not exceed 50 mol % based on the amount of all alcohols used (i.e. sum of trifunctional alcohol and difunctional diol). The amount of dihydric alcohols is preferably not more than 30 mol %, more preferably not more than 20 mol %. Most preferably, only the trifunctional alcohols are used.

The conversion of all components of the hyperbranched polyester can be performed in the presence or absence of a solvent. Suitable solvents are, for example, hydrocarbons such as paraffins, aromatics, ethers and ketones. Preferably, the reaction is, however, performed free of solvent.

The reaction is effected generally at elevated temperatures, for example 30 to 250° C., especially 80 to 220° C. and more preferably 80 to 180° C.

The water or the alcohols formed during the polymerization (polycondensation) should be removed from the reaction medium by means of suitable measures. The reaction can be effected, for example, in the presence of a water-withdrawing agent as an additive which is added at the start of the reaction. Suitable examples are molecular sieves, especially 4 Å molecular sieve, anhydrous $MgSO_4$ or anhydrous $Na_2SO_4$. In addition, water or alcohols formed during the reaction can be distilled off. This can also be done by means of a suitable entraining agent using a water separator. The distillation can preferably be effected under reduced pressure, for example at a pressure of 1 mbar to 500 mbar.

The reaction can be performed in the absence of catalysts. Preference is given, however, to working in the presence of at least one catalyst. The catalysts are preferably acidic inorganic, organometallic or organic catalysts, or mixtures of a plurality of acidic inorganic, organometallic or organic catalysts. It is also possible in accordance with the invention to use enzymes as catalysts, although the use thereof is less preferred.

Acidic inorganic catalysts for the purposes of the present invention are for example sulfuric acid, sulfates and hydrogen sulfates, such as sodium hydrogen sulfate, phosphoric acid, phosphonic acid, hypophosphorous acid, aluminum sulfate hydrate, alum, acidic silica gel (pH≤6, especially ≤5) and acidic aluminum oxide. Further acidic inorganic catalysts which can be used include, for example, aluminum compounds of the general formula $Al(OR^1)_3$ and titanates of the general formula $Ti(OR^1)_4$, it being possible for the radicals $R^1$ to be identical or different in each case and to be selected independently of one another from $C_1$-$C_{20}$ alkyl radicals, such as methyl, ethyl, n-propyl, isopropyl, n-butyl, isobutyl, sec-butyl, tert-butyl, n-pentyl, isopentyl, sec-pentyl, neopentyl, 1,2-dimethylpropyl, isoamyl, n-hexyl, isohexyl, sec-hexyl, n-heptyl, isoheptyl, n-octyl, 2-ethylhexyl, n-nonyl, n-decyl, n-dodecyl, n-hexadecyl or n-octadecyl, for example; $C_3$-$C_{12}$ cycloalkyl radicals, such as cyclopropyl, cyclobutyl, cyclopentyl, cyclohexyl, cycloheptyl, cyclooctyl, cyclononyl, cyclodecyl, cycloundecyl and cyclododecyl, for example; preferably cyclopentyl, cyclohexyl and cycloheptyl. The radicals $R^1$ in $Al(OR^1)_3$ and/or $Ti(OR^1)_4$ are preferably each identical and selected from n-butyl, isopropyl and 2-ethylhexyl.

Preferred acidic organometallic catalysts are chosen for example from dialkyltin oxides $R^1_2SnO$ or dialkyltin diesters $R^1_2Sn(OR^2)_2$ in which $R^1$ is as defined above and can be identical or different. $R^2$ can have the same definitions as $R^1$ and additionally can be $C_6$-$C_{12}$ aryl: phenyl, o-, m- or p-tolyl, xylyl or naphthyl, for example. $R^2$ can in each case be identical or different. Examples of organotin catalysts are tin(II) n-octanoate, tin(II) 2-ethylhexanoate, tin(II) laurate, dibutyltin oxide, diphenyltin oxide, dibutyltin dichloride, dibutyltin diacetate, dibutyltin dilaurate, dibutyltin dimaleate or dioctyltin diacetate. Also conceivable are organoantimony, -bismuth or -aluminum catalysts. Particularly preferred representatives of acidic organometallic catalysts are dibutyltin oxide, diphenyltin oxide and dibutyltin dilaurate.

Preferred acidic organic catalysts are acidic organic compounds containing, for example, phosphate groups, sulfonic acid groups, sulfate groups or phosphonic acid groups. Particular preference is given to sulfonic acids such as para-toluenesulfonic acid, for example. Acidic ion exchangers can also be used as acidic organic catalysts, examples being polystyrene resins which contain sulfonic acid groups and have been crosslinked with about 2 mol % of divinylbenzene.

Combinations of two or more of the aforementioned catalysts can also be employed. A further possibility is to use organic or organometallic or else inorganic catalysts that are in the form of discrete molecules in an immobilized form, on silica gel or on zeolites, for example. If it is desired to use acidic inorganic, organometallic or organic catalysts then the amount of catalyst used is in accordance with the invention from 0.001% to 10% by weight, preferably from 0.01% to 1% by weight.

The reaction time is typically from 5 minutes to 48 hours, preferably from 30 minutes to 24 hours and more preferably from 1 hour to 10 hours. The end of the reaction can often be recognized by the fact that the viscosity of the reaction mixture suddenly starts to rise rapidly. When the viscosity rise begins, the reaction can be stopped, for example by cooling. Thereafter, the carboxyl group number in the (pre) polymer can be determined on a sample of the mixture, for example by titration of the acid number to DIN 53402-2.

The reaction of the monomers described forms ester bonds. The resulting hyperbranched polyesters are essentially uncrosslinked. In the context of this invention, essentially uncrosslinked means that a degree of crosslinking of less than 15% by weight, preferably of less than 10% by weight, determined via the insoluble content of the polymer, is present. The insoluble content of the polymer was determined by extraction for four hours with the same solvent as is used for the gel permeation chromatography, i.e. tetrahydrofuran, dimethylacetamide or hexafluoroisopropanol, according to the solvent in which the polymer has better solubility, in a Soxhlet apparatus and, after drying the residue to constant weight, weighing the remaining residue.

When working without solvent, the end product is generally obtained directly and, if required, can be purified by customary purifying operations. When a solvent has also been used, it can typically be removed from the reaction mixture after the reaction, for instance by vacuum distillation.

The synthesis is notable for its great simplicity and enables the preparation of hyperbranched polyesters in a simple one-pot reaction. The isolation or purification of intermediates or protecting groups for intermediates is not required. Further details of the preparation of hyperbranched polyesters are given, for example, in WO 01/46296, DE 101 63 163, DE 102 19 508, DE 102 40 817 or WO 99/16810. The hyperbranched polyesters are prepared usually within a pressure range from 2 mbar to 20 bar, preferably at standard pressure, in reactors or reactor cascades which are operated batchwise, semicontinuously or continuously. Through the aforementioned establishment of the reaction conditions and optionally through the selection of the suitable solvent, the inventive products can be processed further without further purification after the preparation.

Preference is given to hyperbranched polyesters which have a weight-average molecular weight in the range from about 500 to 100 000, more preferably of 1000 to 50 000. In the case of a hyperbranched polyester joined to one polyalkylene oxide group, the molecular weight relates only to the part of the hyperbranched polyester without the polyalkylene oxide group. The determination is usually effected by gel permeation chromatography with a refractometer as the detector. Preference is given to performing the determination as described in the examples.

The polydispersity of the polyesters used in accordance with the invention is generally from 1.2 to 50, preferably from 1.4 to 40, more preferably from 1.5 to 30 and most preferably from 2 to 30. The polydispersity data and the number-average and weight-average molecular weight data $M_n$ and $M_w$ are based here on gel permeation chromatography analyses, using polymethyl methacrylate as the standard and tetrahydrofuran, dimethylacetamide or hexafluoroisopropanol as the eluent. The method is described in Analytiker Taschenbuch [Analyst's Handbook], Volume 4, pages 433 to 442, Berlin 1984.

The type of terminal groups can be influenced by the ratio of the monomers used. If predominantly OH-terminated polymers are to be obtained, the alcohols should be used in excess. If predominantly COOH-terminated polymers are to be obtained, the carboxylic acids should be used in excess.

The number of free OH groups (hydroxyl number) of the hyperbranched polyester is generally from 10 to 500 mg, preferably from 20 to 450 mg of KOH per gram of polymer and can be determined, for example, by titration to DIN 53240-2.

The number of free COOH groups (acid number) of the hyperbranched polyester is generally from 0 to 400, preferably from 25 to 300, even more preferably 50 to 250 and especially 120 to 250 mg KOH per gram of polymer and can likewise be determined by titration to DIN 53402.

The hyperbranched polyesters used in accordance with the invention generally have at least 4 functional groups. There is in principle no upper limit in the number of functional groups. However, products having too high a number of functional groups frequently have undesired properties, for example poor solubility or a very high viscosity. The hyperbranched polymers used in accordance with the invention therefore generally have not more than 100 functional groups. The hyperbranched polymers preferably have from 6 to 50 and more preferably from 6 to 30 functional groups.

The hyperbranched polyester is preferably joined to a polyalkylene oxide group and/or a functional $C_1$-$C_{24}$ end group comprising one acid group or two alcohol groups. The hyperbranched polyester is more preferably joined to a polyalkylene oxide group. As a result of this, nonionic amphiphilic solubilizers may be obtained, since (partial) neutralization of the carboxylic acid groups is no longer necessary to achieve water solubility/water dispersibility.

These nonionic solubilizers are particularly suitable for producing active ingredient formulations with long-term stability.

Examples of a polyalkylene oxide group are polyethylene glycol or polyethylene glycol monoalkyl ethers with a molar mass Mn of 200 to 10 000 g/mol, preferably 300-2000 g/mol. The polyethylene glycol is preferably a polyethylene glycol mono-$C_1$-$C_{18}$-alkyl ether, especially a polyethylene glycol monomethyl ether.

The hyperbranched polyester is preferably joined to the polyalkylene oxide group by means of a polyisocyanate linker.

The linker-reactive group used may be a hydroxyl group at the chain end of the polyalkylene oxide group. Preference is given to polyethylene glycol monoalkyl ethers which have exactly one linker-reactive group at the chain end. Suitable polyisocyanate linkers are polyisocyanates with a functionality based on the isocyanate groups of at least 1.5, particularly 1.5 to 4.5 and especially 1.8 to 3.5, comprising aliphatic, cycloaliphatic and aromatic di- and polyisocyanates, and the isocyanurates, allophanates, uretdiones and biurets of aliphatic, cycloaliphatic and aromatic diisocyanates. The polyisocyanates preferably have an average of 1.8 to 3.5 isocyanate groups per molecule. Examples of suitable polyisocyanates are aromatic diisocyanates such as toluene 2,4-diisocyanate, toluene 2,6-diisocyanate, commercially available mixtures of toluene 2,4- and 2,6-diisocyanate (TDI), n-phenylene diisocyanate, 3,3'-diphenyl-4,4'-biphenylene diisocyanate, 4,4'-biphenylene diisocyanate, 4,4'-diphenylmethane diisocyanate, 2,4'-diphenylmethane diisocyanate, 3,3'-dichloro-4,4'-biphenylene diisocyanate, cumene 2,4-diisocyanate, 1,5-naphthalene diisocyanate, p-xylylene diisocyanate, p-phenylene diisocyanate, 4-methoxy-1,3-phenylene diisocyanate, 4-chloro-1,3-phenylene diisocyanate, 4-ethoxy-1,3-phenylene diisocyanate, 2,4-dimethylene-1,3-phenylene diisocyanate, 5,6-dimethyl-1,3-phenylene diisocyanate, 2,4-diisocyanatodiphenyl ether, aliphatic diisocyanates such as ethylene diisocyanate, ethylidene diisocyanate, propylene 1,2-diisocyanate, 1,6-hexamethylene diisocyanate (HDI), 1,4-tetramethylene diisocyanate, 1,10-decamethylene diisocyanate, and cycloaliphatic diisocyanates such as isophorone diisocyanate (IPDI), cyclohexylene 1,2-diisocyanate, cyclohexylene 1,4-diisocyanate and bis(4,4'-isocyanatocyclohexyl)methane. Among the polyisocyanates, preference is given to those whose isocyanate groups differ in terms of reactivity, such as toluene 2,4-diisocyanate, toluene 2,6-diisocyanate, 4'-diphenylmethane diisocyanate, cis- and trans-isophorone diisocyanate, or mixtures of these compounds.

The reaction with the polyisocyanate linker is effected in the melt or in an organic solvent, preferably in an aprotic polar organic solvent or in mixtures of such solvents. Examples are ketones (for example acetone), butyl acetate, tetrahydrofuran (THF), xylene, chlorobenzene, dimethyl sulfoxide (DMSO) or dimethylformamide (DMF). Preferred solvents are butyl acetate, xylene and acetone. The reaction is effected typically at elevated temperatures, the temperature also being guided by the boiling temperature of the solvent selected. The reaction of the polyisocyanate linker with the first component can be effected at 20 to 80° C., but if desired also up to 100° C. The reaction of the further isocyanate group can be effected at temperatures of 50 to 100° C. The solvent can subsequently be removed by distillation.

The reaction can be effected in an equimolar manner, which means that the quantitative ratio is selected such that 1 mol of diisocyanate is used per mole of hydroxyl groups of the functionalizing reagent or of the linear polyalkylene oxide to be converted. Preference is given to working with a slight (e.g. 0 to 15 mol %) excess of the hydroxyl groups, in order to reduce the amount of unconverted diisocyanate. In the case of symmetric diisocyanates (such as HDI), it may also be advisable to use an excess of diisocyanate and to remove the excess subsequently by distillation.

Preference is given to performing the reaction in the presence of a catalyst. Suitable catalysts are, for example, tertiary amines, for example triethylamine, tri-n-propylamine, N-methylpyrrolidine, N-methylpiperidine and diazabicyclooctane (DABCO), zinc carboxylates, bismuth carboxylates, titanium alkoxides, organotin compounds, especially dialkyltin(IV) salts of aliphatic carboxylic acids such as dibutyltin dilaurate and dibutyltin dioctoate, tin(II) dialkoxides such as tin dioctoate, and cesium salts such as cesium acetate. In one embodiment, tin carboxylates, bismuth carboxylates, titanium alkoxides are particular suitable, the carboxylates preferably being $C_1$-$C_{20}$ carboxylates (such as formate, acetate, propionate, hexanoate, octanoate or neodecanoate). The catalyst can be used in amounts of 50 to 50 000 ppm, preferably 100 to 5000 ppm, based on all of the solids.

Typically, the reaction will be performed in such a way that the component which is to be functionalized with isocyanate groups (for example the polyalkylene oxide) is first reacted with the diisocyanate in the presence of the catalyst and of a solvent until the isocyanate value in the reaction mixture has fallen by half. When a slight hydroxyl group excess is used, conversion is continued until the theoretical end value corresponds to the complete conversion of the hydroxyl groups. This can be determined in a known manner, for example by titrimetric means. This is then followed by the addition of the hyperbranched polyester. The molar ratio of hyperbranched polyester to the polyalkylene oxide or to the functional $C_1$-$C_{24}$ end group comprising one acid group or two alcohol groups is 1:1 to 1:25, preferably 1:2 to 1:15. The reaction is continued until the isocyanate value has fallen to zero.

Suitable functional $C_1$-$C_{24}$ end groups comprising one acid group or two alcohol groups are preferably aliphatic compounds which have 1-24 carbon atoms and bear at least one acid group or at least two alcohol groups. Acid groups are, for example, a carboxylic acid group, a sulfonic acid group, a sulfenic acid group, a sulfinic acid group, a sulfuric ester group (i.e. an organic sulfate), a phosphoric acid group, an amino group or at least two hydroxy-$C_2$-$C_{10}$-alkyl groups, more preferably a carboxylic acid group. Optionally, the functional $C_1$-$C_{24}$ unit may also comprise more than one of the groups listed at the same time. The functional $C_1$-$C_{24}$ end group is preferably based on a cyclic carboxylic anhydride, and is especially succinic anhydride. Some or all of the acid groups of the functional $C_1$-$C_{24}$ end group may be neutralized, preferably with alkali metal hydroxides or organic amines.

In one embodiment, the functional $C_1$-$C_{24}$ unit additionally comprises a joining group with which the functional $C_1$-$C_{24}$ units can be joined covalently to the hyperbranched polyester, directly or by means of a polyisocyanate linker. Suitable joining groups can react with the OH and/or carboxylic acid groups of the polyester. Examples are carboxylic acids, carboxylic esters, carboxylic anhydrides, isocyanates, amines and alcohols. Further suitable joining groups can react with the polyisocyanate linker. Examples are alcohols or amines, preferably alcohols.

The hyperbranched polyester which is joined to functional $C_1$-$C_{24}$ end groups is typically obtainable, and is preferably obtained, by reacting the hyperbranched polyester with a functionalizing reagent which comprises the functional $C_1$-$C_{24}$ unit comprising one acid group, one amino group or at least two hydroxyl groups and the linking group, and optionally with a polyisocyanate linker.

Suitable functionalizing reagents for direct covalent joining without linkers are anhydrides. Particularly suitable are cyclic carboxylic anhydrides, such as succinic anhydride or phthalic anhydride, especially succinic anhydride. The anhydrides are typically reacted with the hyperbranched polyester at elevated temperatures, usually 80 to 200° C. The reaction can be effected with or without addition of solvents. Further purification is not normally necessary.

Suitable functionalizing reagents for covalent joining by means of polyisocyanate linkers are hydroxycarboxylic acids, aminocarboxylic acids, hydroxysulfonic acids, hydroxysulfates, aminosulfonic acids or aminosulfates, hydroxyamines (such as diethanolamine), polyamines (e.g. diethylenetetramine), or polyols (e.g. glycerol, trimethylolpropane, pentaerythritol). Preferred polyisocyanate linkers for this purpose are diisocyanates, more preferably aliphatic diisocyanates (such as hexamethylene diisocyanate and isophorone diisocyanate).

The inventive composition is obtainable by contacting the hyperbranched polyester and the active ingredient which has a maximum solubility in water at 20° C. of 10 g/l. The components can be contacted by commonly known methods, such as mixing, emulsifying or suspending.

The weight ratio of hyperbranched polyester to active ingredient is usually in the range from 1:50 to 100:1, preferably 1:5 to 50:1, more preferably 1:2 to 25:1. The active ingredient may be present in dissolved form or in solid particulate form. The active ingredient particles may be crystalline or amorphous. The particle size may be 1 nm to 10 µm.

The composition may be in the form of a solid, solution, emulsion, suspension or suspoemulsion of the active ingredient. The inventive composition is preferably an aqueous composition. In a further preferred embodiment, the inventive composition is a solid, and is more preferably a solid solution. In the case of solid solutions, the active ingredient is typically in amorphous form, dispersed in a polymer matrix.

It preferably comprises at least 40% by weight, more preferably at least 60% by weight and especially at least 80% by weight of water. The composition typically comprises at most 99% by weight of water.

The inventive composition may comprise formulating assistants, the selection of the assistants typically being guided by the specific application form and the active ingredient. Examples of suitable formulating assistants are solvents, solid carriers, surfactants (including protective colloids, wetters and stickers), organic and inorganic thickeners, bactericides, antifreezes, defoamers, and optionally dyes and adhesives (for example for seed treatment).

Useful surfactants (adjuvants, wetters, stickers, dispersants or emulsifiers) include the alkali metal, alkaline earth metal, ammonium salts of aromatic sulfonic acids, for example of lignosulfonic acid (Borresperseproducts, Borregaard, Norway), phenolsulfonic acid, naphthalenesulfonic acid, (Morwet® products, Akzo Nobel, USA) and dibutylnaphthalenesulfonic acid (Nekal® products, BASF, Germany), and also of fatty acids, alkyl- and alkylarylsulfonates, alkyl ether, lauryl ether and fatty alcohol sulfates, and salts of sulfated hexa-, hepta- and octadecanols, and of fatty alcohol glycol ethers, condensation products of sulfonated naphthalene and derivatives thereof with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenyl and tributylphenyl polyglycol ethers, alkylaryl polyether alcohols, isotridecyl alcohol, fatty alcohol ethylene oxide condensates, ethoxylated castor oil, polyoxyethylene or polyoxypropylene alkyl ethers, lauryl alcohol polyglycol ether acetate, sorbitol esters, lignosulfite waste liquors and proteins, denatured proteins, polysaccharides (e.g. methylcellulose), hydrophobically modified starches, polyvinyl alcohol (Mowiol® products, Clariant, Switzerland), polycarboxylates (Sokalan® products, BASF, Germany), polyalkoxylates, polyvinylamine (Lupamin® products, BASF, Germany), polyethyleneimine (Lupasol® products, BASF, Germany), polyvinylpyrrolidone and copolymers thereof.

In a preferred embodiment, the active ingredient is a pesticide and the inventive compositions are in the form of an agrochemical formulation. Suitable agrochemical formulations are water-soluble concentrates (SL, LS), redispersible concentrates (DC), emulsifiable concentrates (EC), emulsions (EW, EO, ES, ME), suspensions (SC, OD, FS) or suspoemulsions (SE). The composition is preferably in the form an emulsifiable concentrate (EC), of a suspension concentrate (SC), of a water-soluble concentrate (SL), of a solution for seed treatment (LS), or of a redispersible concentrate (DC).

The agrochemical formulation is usually diluted before use in order to produce the so-called tankmix. Useful substances for dilution include mineral oil fractions of moderate to high boiling point, such as kerosene or diesel oil, and also coal tar oils and oils of vegetable or animal origin, aliphatic, cyclic and aromatic hydrocarbons, for example toluene, xylene, paraffin, tetrahydronaphthalene, alkylated naphthalenes or derivatives thereof, methanol, ethanol, propanol, butanol, cyclohexanol, cyclohexanone, isophorone, highly polar solvents, for example dimethyl sulfoxide, N-methylpyrrolidone or water. Preference is given to using water. It is also possible not to add the amphiphile until the tankmix stage. In this embodiment, the inventive composition is present in the form of a tankmix.

The diluted composition is typically applied by spraying or nebulizing. Immediately before application (tankmix), it is possible to add to the tankmix oils of various types, wetters, adjuvants, herbicides, bactericides, fungicides. These agents can be added to the inventive compositions in a weight ratio of 1:100 to 100:1, preferably 1:10 to 10:1. The pesticide concentration in the tankmix can be varied within relatively wide ranges. In general, it is between 0.0001 and 10%, preferably between 0.01 and 1%. The application rates in the case of application in crop protection, according to the type of effect desired, are between 0.01 and 2.0 kg of active ingredient per ha.

The use of the agrochemical formulations is possible for control of phytopathogenic fungi and/or undesired plant growth and/or undesired insect or mite infestation and/or for regulation of the growth of plants, by allowing the composition to act on the particular pests, the habitat thereof or the plants to be protected from the particular pest, the soil and/or undesired plants and/or the crop plants and/or the habitat thereof. In addition, it is possible to use the agrochemical formulations to control undesired insect or mite infestation on plants and/or to control phytopathogenic fungi and/or to control undesired plant growth, by treating seeds of crop plants with the composition.

The invention also relates to a hyperbranched polyester based on a hydrophobic dicarboxylic acid and a trifunctional alcohol, wherein the hydrophobic dicarboxylic acid is an aliphatic $C_{10}$-$C_{32}$ dicarboxylic acid, a dicarboxylic acid having a polyisobutylene group and/or a succinic acid unit having a $C_3$-$C_{40}$ group, and the trifunctional alcohol is glycerol, trimethylolethane, trimethylolpropane, bis(trimethylolpropane), pentaerythritol, or an ethoxylated or propoxylated derivative thereof, and wherein the hyperbranched polyester is joined to a polyalkylene oxide group and/or a functional $C_1$-$C_{24}$ end group comprising one acid group or two alcohol groups. Suitable and preferred embodiments of the hyperbranched polyester are as described above.

The invention further relates to a process for preparing the inventive hyperbranched polyester, by polycondensing the hydrophobic dicarboxylic acid and the trifunctional alcohol, and then joining the product to a polyalkylene oxide group and/or a functional $C_1$-$C_{24}$ end group comprising one acid group or two alcohol groups. Optionally, some or all of the acid groups of the functional $C_1$-$C_{24}$ end group may be neutralized, preferably with alkali metal hydroxides or organic amines.

The invention further relates to the use of the inventive hyperbranched polyester for solubilizing an active ingredient which has a maximum solubility in water at 20° C. of 10 g/l in aqueous solutions. "Solubilization" means that more active ingredient can be brought into solution in the presence of the hyperbranched polyester than in the absence thereof under otherwise identical conditions. It is preferably possible to bring at least twice the amount, more preferably at least five times the amount and especially ten times the amount into solution.

Advantages of the present invention are that a high concentration of active ingredient can be brought into solution; that the preparation of the amphiphile from commercially readily available monomers can be accomplished very easily and industrially, optionally even in a one-pot process. A further advantage is that the amphiphile itself is water-soluble or water-dispersible, and that it is less sensitive to hydrolysis than are many polyesters. Further advantages are that the bioavailability of the active ingredients is increased, that the systemic effect of the active agrochemical ingredients is increased on foliar uptake, that even sparingly soluble active agrochemical ingredients can now be formulated in solution, for example as an SL (water-soluble concentrate) or LS (solution for seed treatment), that the distribution of the active agrochemical ingredients in the spraying solution is improved, and that the multiple-use packaging of the active ingredients, and the application equipment (e.g., the spraying equipment for pesticides), can be cleaned more effectively with water.

The examples which follow illustrate the invention without restricting it.

EXAMPLES

The general name "TMP×n EO/PO" (e.g. "TMP×1.1 PO" or "TMP×12.2 EO") describes a product which, per mole of trimethylolpropane, has been reacted with an average of n mol (e.g. 1.1 mol) of propylene oxide (PO) or ethylene oxide (EO). PIBSA 1000 describes a polyisobutylene (M=1000 g/mol) with a terminal succinic anhydride group. Pentasize 8 and Pentasize 68 are understood to mean commercially available alkenylsuccinic anhydrides (Trigon Chemie), wherein the alkenyl radicals are unsaturated C18 units (Pentasize 8) or a mixture of C16/C18 units (Pentasize 68). DBTL is the abbreviation of the di-n-butyltin dilaurate catalyst.

The hyperbranched polymers were analyzed by gel permeation chromatography with a refractometer as the detector. The mobile phase used was THF; the standard used to determine the molecular weight was polymethyl methacrylate (PMMA). The acid number was determined in each case to DIN 53402. The OH number (mg KOH/g) was determined on the basis of DIN 53240, part 2.

The molar masses of the polyesters functionalized with a polyalkylene oxide group were determined by calculation from the number-average molecular weight of the parent hyperbranched core, the OH number thereof and the degree of functionalization selected (stoichiometric ratio of NCO groups of the functional linear polymers to the available hydroxyl groups of the core molecule).

Synthesis Example 1: Hyperbranched Polyester A.1

A four-neck flask provided with stirrer, internal thermometer, nitrogen inlet tube and descending condenser with collecting vessel was initially charged with 120.1 g of trimethylolpropane and 380.1 g of sebacic acid, which were sparged with dry nitrogen, and the reaction mixture was heated to 160-170° C. while stirring. After a reaction time of 1.5 h, in which 32 ml of water had separated out (conversion 47%), the reaction was ended by cooling to room temperature. The polymer A.1 (Mn=980 g/mol; Mw=22 230 g/mol; OH number: 79 mg KOH/g polymer; acid number: 182 mg KOH/g polymer) was obtained in the form of a yellow liquid of high viscosity, which, after neutralization of 75% of the terminal carboxylic acid groups with triethanolamine, had very good water solubility. The polymer A.1 was used in this partly neutralized form for the further experiments.

Synthesis Example 2: Hyperbranched Polyester A.2

In a four-neck flask provided with stirrer, internal thermometer, nitrogen inlet tube and descending condenser with a collecting vessel, an initial charge of 194.6 g of the trifunctional alcohol TMP×3.2 EO and 305.5 g of sebacic acid sparged with dry nitrogen was admixed with 0.2 g of DBTL, and the reaction mixture was heated to 160-170° C. while stirring. After a reaction time of 2 h, in which 26 ml of water had separated out (conversion 47%), the reaction was ended by cooling to room temperature. The polymer A.2 (Mn=960 g/mol; Mw=9520 g/mol; OH number: 48 mg KOH/g polymer; acid number: 156 mg KOH/g polymer) was obtained in the form of a yellow liquid of high viscosity, which, after neutralization of 100% of the terminal carboxylic acid groups with triethanolamine, had very good water solubility. The polymer A.2 was used in this completely neutralized form for the further experiments.

Synthesis Example 3: Hyperbranched Polyester A.3

In a four-neck flask provided with stirrer, internal thermometer, nitrogen inlet tube and descending condenser with a collecting vessel, an initial charge of 160.4 g of the trifunctional alcohol TMP×1.1 PO and 340.2 g of sebacic acid sparged with dry nitrogen was admixed with 0.2 g of DBTL, and the reaction mixture was heated to 160° C. while stirring. After 4 h, in which 24 ml of water separated out (conversion 39%), the reaction was ended by cooling to room temperature.

The polymer A.3 (Mn=820 g/mol; Mw=6140 g/mol; OH number: 70 mg KOH/g polymer; acid number: 169 mg KOH/g polymer) was obtained in the form of a yellow liquid of high viscosity, which, after neutralization of 100% of the terminal carboxylic acid groups with triethanolamine, had very good water solubility. The polymer A.3 was used in this completely neutralized form for the further experiments.

Synthesis Example 4: Hyperbranched Polyester A.4

In a four-neck flask provided with stirrer, internal thermometer, nitrogen inlet tube and descending condenser with collecting vessel, an initial charge of 371.9 g of the trifunctional alcohol TMP×12.2 EO and 230.7 g of alkenylsuccinic anhydride (Pentasize 8) sparged with dry nitrogen was admixed with 0.3 g of DBTL, and the reaction mixture was heated to 180-200° C. while stirring. After a reaction time of 7 h, the reaction was ended by cooling to room temperature. The polymer A.4 ($Mn=3850$ g/mol; $Mw=38\,070$ g/mol; OH number: 73 mg KOH/g polymer; acid number: 27 mg KOH/g polymer) was obtained in the form of a yellow liquid of high viscosity, which, even without neutralization of the terminal carboxylic acid groups, had very good water solubility. The polymer A.4 was used in this completely protonated form for the further experiments.

Synthesis Example 5: Hyperbranched Polyester A.5

In a four-neck flask provided with stirrer, internal thermometer, nitrogen inlet tube and descending condenser with a collecting vessel, an initial charge of 228.8 g of the trifunctional alcohol TMP×12.2 EO, 34.1 g of polyethylene glycol monomethyl ether ($M=500$ g/mol), 204.9 g PIBSA 1000 and 32.2 g of succinic acid sparged with dry nitrogen was admixed with 0.2 g of DBTL, and the reaction mixture was heated to 160-180° C. while stirring. After 2 h, the reaction was ended by cooling to room temperature. The polymer A.5 ($Mn=1540$ g/mol; $Mw=5200$ g/mol; OH number: 65 mg KOH/g polymer; acid number: 32 mg KOH/g polymer) was obtained in the form of a yellow liquid of high viscosity, which, even without neutralization of the terminal carboxylic acid groups, had very good water solubility. The polymer A.5 was used in this completely protonated form for the further experiments.

Synthesis Example 6: Hyperbranched Polyester A.6

In a four-neck flask provided with stirrer, internal thermometer, nitrogen inlet tube and descending condenser with a collecting vessel, an initial charge of 253.8 g of the trifunctional alcohol TMP×12.2 EO, 227.3 g of PIBSA 1000 and 19.0 g of succinic anhydride sparged with dry nitrogen was admixed with 0.2 g of DBTL, and the reaction mixture was heated to 180-200° C. while stirring. After 3.5 h, the reaction was ended by cooling to room temperature. The polymer A.6 ($Mn=2700$ g/mol; $Mw=7000$ g/mol; OH number: n.d.; acid number: 22 mg KOH/g polymer) was obtained in the form of a yellow liquid of high viscosity, which, even without neutralization of the terminal carboxylic acid groups, had very good water solubility. The polymer A.6 was used in this completely protonated form for the further experiments.

Synthesis Example 7: Hyperbranched Polyester A.7

In a four-neck flask provided with stirrer, internal thermometer, nitrogen inlet tube and descending condenser with a collecting vessel, an initial charge of 270.11 g of the trifunctional alcohol TMP×3.2 EO, 282.8 g of sebacic acid and 245.1 g of alkenylsuccinic anhydride (Pentasize 8) sparged with dry nitrogen was admixed with 0.2 g of DBTL, and the reaction mixture was heated to 160-170° C. while stirring. After 3.5 h, in which 20 ml of water separated out (conversion 26%), the reaction was ended by cooling to room temperature. The polymer A.7 ($Mn=1240$ g/mol; $Mw=8290$ g/mol; OH number: 52 mg KOH/g polymer; acid number: 134 mg KOH/g polymer) was obtained in the form of a yellow liquid of high viscosity, which, after neutralization of 75% of the terminal carboxylic acid groups with triethanolamine, had very good water solubility. The polymer A.7 was used in this partly neutralized form for the further experiments.

Synthesis Example 8: Hyperbranched Polyester with Increased Acid Number A.8

In a four-neck flask provided with stirrer, internal thermometer, nitrogen inlet tube and descending condenser with a collecting vessel, an initial charge of 194.6 g of the trifunctional alcohol TMP×3.2 EO and 305.5 g of sebacic acid sparged with dry nitrogen was admixed with 0.2 g of DBTL, and the reaction mixture was heated to 160-170° C. while stirring. After 2 h, in which 26 ml of water separated out (conversion 47%), the mixture was cooled to room temperature. 102.6 g of the product thus obtained were admixed with 2.7 g of succinic anhydride and the mixture was heated to 130° C. After 2 h, the mixture was cooled to 60° C. and the succinic anhydride sublimed in the condenser was returned back to the reaction by adding 50 g of acetone. While distilling off the acetone, the reaction mixture was heated slowly up to 110° C. over the course of 3 h. Then the reaction was ended by cooling to room temperature. The polymer A.8 ($Mn=1190$ g/mol; $Mw=46\,650$ g/mol; OH number: 27 mg KOH/g polymer; acid number: 154 mg KOH/g polymer) was obtained in the form of a yellow liquid of high viscosity, which, after neutralization of 100% of the terminal carboxylic acid groups with triethanolamine, had very good water solubility. The polymer A.8 was used in this completely neutralized form for the further experiments.

Synthesis Example 9: Hyperbranched Polyester with Increased Acid Number A.9

In a four-neck flask provided with stirrer, internal thermometer, nitrogen inlet tube and descending condenser with a collecting vessel, an initial charge of 1290.0 g of the trifunctional alcohol TMP×5.2 PO and 1047.0 g of alkenylsuccinic anhydride (Pentasize 8) sparged with dry nitrogen was admixed with 0.2 g of DBTL. The reaction mixture was, heated to 160-180° C. while stirring, and stirred at this temperature at a vacuum of 50 mbar for 13 h. Then the reaction was ended by cooling to room temperature. 536.7 g of the product thus obtained were admixed with 70.1 g of succinic anhydride, and the mixture was heated to 130° C. After 2 h, it was cooled to 60° C. and the succinic anhydride sublimed in the condenser was returned back to the reaction by adding 45 g of acetone. While distilling off the acetone, the reaction mixture was heated slowly up to 130° C. over 1 h. Then it was cooled to room temperature. The polymer A.9 ($Mn=2430$ g/mol; $Mw=9170$ g/mol; OH number: 18 mg KOH/g polymer; acid number: 92 mg KOH/g polymer) was obtained in the form of a yellow liquid of high viscosity, which, after neutralization of 50% of the terminal carboxylic acid groups with triethanolamine, had very good water solubility. The polymer A.9 was used in this partly neutralized form for the further experiments.

Synthesis Example 10: Hyperbranched Polyester with Increased Acid Number A.10

In a four-neck flask provided with stirrer, internal thermometer, nitrogen inlet tube and descending condenser with a collecting vessel, an initial charge of 270.11 g of the trifunctional alcohol TMP×3.2 EO, 282.8 g of sebacic acid and 245.1 g of alkenylsuccinic anhydride (Pentasize 8) sparged with dry nitrogen was admixed with 0.2 g of DBTL, and the reaction mixture was heated to 160-170° C. while stirring. After a reaction time of 3.5 h, in which 20 ml of water separated out (conversion 26%), the reaction was ended by cooling to room temperature. 209.6 g of the product thus obtained were admixed with 5.8 g of succinic anhydride, and the mixture was heated to 130° C. After 2 h, the mixture was cooled and the succinic anhydride sublimed in the condenser was returned back to the reaction by adding 42 g of acetone. While distilling off the acetone, the reaction mixture was heated slowly to 100° C. over 1 h. Then it was cooled to room temperature. The polymer A.10 ($Mn=1240$ g/mol; $Mw=14\,120$ g/mol; OH number: 34 mg KOH/g polymer; acid number: 147 mg KOH/g polymer) was obtained in the form of a yellow liquid of high viscosity, which, after neutralization of 75% of the terminal carboxylic acid groups with triethanolamine, had very good water solubility. The polymer A.10 was used in this partly neutralized form for the further experiments.

Synthesis Example 11: Hyperbranched Polyester Core (A.11a) with a Shell of Linear PEG Chains, 100% Functionalization, A.11

Stage 1a: Preparation of a Hyperbranched Polyester A.11a

In a four-neck flask provided with stirrer, internal thermometer, nitrogen inlet tube and descending condenser with a collecting vessel, an initial charge of 251.7 g of the trifunctional alcohol TMP×5.2 PO and 248.3 g of sebacic acid sparged with dry nitrogen was admixed with 0.3 g of DBTL catalyst, and the reaction mixture was heated to 160-180° C. while stirring. After a reaction time of 8.5 h, in which 16 ml of water separated out (conversion 36%), the reaction was ended by cooling to room temperature. The polymer A.11a ($Mn=1110$ g/mol; $Mw=9990$ g/mol; OH number: 49 mg KOH/g polymer; acid number: 124 mg KOH/g polymer) was obtained in the form of a yellow liquid of high viscosity, which was not water-soluble.

Stage 1b (A.11b):

70.0 g of polyethylene glycol monomethyl ether ($Mn=750$ g/mol) were initially charged in a 250 ml three-neck flask equipped with a reflux condenser and an internal thermometer, and freed of water residues at 80° C. under reduced pressure. After cooling to room temperature, the mixture was placed under nitrogen, and the polymer was dissolved in 70.0 g of n-butyl acetate. Then 20.2 g of isophorone diisocyanate (IPDI) were added and the mixture was heated to 50° C. Addition of 11 mg of zinc neodecanoate (Tegokat 616, TIB Chemicals, Mannheim), dissolved in 1 ml of n-butyl acetate started the reaction, which was conducted over the course of approx. 12 h at 50° C. until an NCO content of 2.12%. Subsequently, the reaction was ended by cooling to −20° C. The reaction product A.11b was used directly without further workup in stage 2.

Stage 2 (A.11):

25.0 g of the hyperbranched polyester core A.11a were dissolved in 10 g of tetrahydrofuran in a 250 ml three-neck flask equipped with a reflux condenser and an internal thermometer, and admixed with 51.0 g of the reaction mixture A.11b under nitrogen. Then the mixture was heated to 60° C., and the reaction was started by adding 5 mg of DBTL dissolved in 1 ml of n-butyl acetate. After the complete conversion of all NCO groups (NCO content 0%), the mixture was cooled and the solvent was removed under reduced pressure. Finally, the linear dendritic copolymer A.11 ($Mn=1860$ g/mol) was obtained in the form of a yellow liquid of high viscosity, which was completely water-soluble.

Synthesis Example 12: Hyperbranched Polyester Core (A.12a) with a Shell Composed of Linear PEG Chains, 50% Functionalization, A.12

Stage 1a: Preparation of a Hyperbranched Polyester, A.12a

In a four-neck flask provided with stirrer, internal thermometer, nitrogen inlet tube and descending condenser with a collecting vessel, an initial charge of 200.0 g of trimethylolpropane and 300.7 g of sebacic acid sparged with dry nitrogen was admixed with 0.1 g of DBTL catalyst, and the reaction mixture was heated to 160-180° C. while stirring. After a reaction time of 105 min, in which 39 ml of water separated out (conversion 72%), the reaction was ended by cooling to room temperature. The polymer A.12a ($Mn=1410$ g/mol; $Mw=34\,520$ g/mol; OH number: 210 mg KOH/g polymer; acid number: 40 mg KOH/g polymer) was obtained in the form of a yellow liquid of high viscosity, which was not water-soluble.

Stage 1b (A.12b):

280.0 g of polyethylene glycol monomethyl ether ($Mn=500$ g/mol) were initially charged in a 1000 ml three-neck flask equipped with a reflux condenser and an internal thermometer, and freed of water residues at 80° C. under reduced pressure. After cooling to room temperature, the mixture was placed under nitrogen and the polymer was dissolved in 280.0 g of n-butyl acetate. Then 111.0 g of IPDI were added and the mixture was heated to 50° C. Addition of 42 mg of zinc neodecanoate dissolved in 1 ml of n-butyl acetate started the reaction, which was conducted over the course of 5.5 h at 50° C. until an NCO content of 2.79%. Subsequently, the reaction was ended by cooling to −20° C. The reaction product A.12b was used directly in stage 2 without further workup.

Stage 2 (A.12):

18.0 g of the hydrophobic hyperbranched polyester core A.12a were initially charged in a 250 ml three-neck flask equipped with a reflux condenser and an internal thermometer, and admixed under nitrogen with 50.6 g of the reaction mixture A.12b. The mixture was then heated to 80° C. and the reaction was started by adding 5 mg of DBTL dissolved in 1 ml of n-butyl acetate. After the complete conversion of all NCO groups (NCO content 0%), the mixture was cooled and the solvent was removed under reduced pressure. Finally, the linear dendritic copolymer A.12 ($Mn=2700$ g/mol) was obtained in the form of a yellow liquid of high viscosity, which was completely water-soluble.

Synthesis Example 13: Hyperbranched Polyester Core (A.13a) with a Shell Composed of Linear PEG Chains, 100% Functionalization, A.13

Stage 1a: Preparation of a Hyperbranched Polyester, A.13a

In a four-neck flask provided with stirrer, internal thermometer, nitrogen inlet tube and descending condenser with a collecting vessel, an initial charge of 222.9 g of the trifunctional alcohol TMP×3.2 EO and 277.3 g of Pentasize 68 sparged with dry nitrogen was admixed with 0.2 g of DBTL, and the reaction mixture was heated to 200° C. while stirring. After a reaction time of 6 h, the reaction was ended by cooling to room temperature. The polymer A.13a (Mn=1990 g/mol; Mw=123 860 g/mol; OH number: 41 mg KOH/g polymer; acid number: 18 mg KOH/g polymer) was obtained in the form of a yellow liquid of high viscosity, which was not water-soluble.

Stage 1b (A.13b):

50.0 g of polyethylene glycol monomethyl ether (Mn=1000 g/mol) were initially charged in a 250 ml three-neck flask equipped with a reflux condenser and an internal thermometer, and freed of water residues at 80° C. under reduced pressure. After cooling to room temperature, the mixture was placed under nitrogen and the polymer was dissolved in 50.0 g of n-butyl acetate. Then 10.1 g of isophorone diisocyanate (IPDI) were added and the mixture was heated to 50° C. Addition of 8 mg of zinc neodecanoate dissolved in 1 ml of n-butyl acetate started the reaction, which was conducted over the course of 4.5 h at 50° C. until an NCO content of 1.43%. Subsequently, the reaction was ended by cooling to −20° C. The reaction product A.13b was used directly in stage 2 without further workup.

Stage 2 (A.13):

6.0 g of A.13a were dissolved in 54.0 g of n-butyl acetate in a 250 ml three-neck flask equipped with a reflux condenser and an internal thermometer, and admixed under nitrogen with 12.9 g of the reaction mixture A.13b. Then the mixture was heated to 80° C. and the reaction was started by adding 2 mg of DBTL dissolved in 1 ml of n-butyl acetate. After the complete conversion of all NCO groups (NCO content 0%), the mixture was cooled and the solvent was removed under reduced pressure. Finally, the linear dendritic copolymer A.13 (Mn=3390 g/mol) was obtained in the form of a yellow liquid of high viscosity, which was completely water-soluble.

Synthesis Example 14: Hyperbranched Polyester Core (A.14a) with a Shell of Linear PEG Chains, 100% Functionalization, A.14

Stage 1a: Preparation of a Hyperbranched Polyester, A.14a

In a four-neck flask provided with stirrer, internal thermometer, nitrogen inlet tube and descending condenser with a collecting vessel, an initial charge of 70.3 g of the trifunctional alcohol TMPx1.1 PO, 84.1 g of sebacic acid and 347.2 g of PIBSA 1000 sparged with dry nitrogen was admixed with 0.1 g of DBTL catalyst, and the reaction mixture was heated to 160-165° C. while stirring. After a reaction time of 2.5 h, the reaction was ended by cooling to room temperature. The polymer A.14a (Mn=1450 g/mol; Mw=4750 g/mol; OH number: 56 mg KOH/g polymer; acid number: 68 mg KOH/g polymer) was obtained in the form of a yellow liquid of high viscosity, which was not water-soluble.

Stage 1b (A.14b):

61.8 g of polyethylene glycol monomethyl ether (Mn=500 g/mol) were initially charged in a 250 ml three-neck flask equipped with a reflux condenser and an internal thermometer, and freed of water residues at 80° C. under reduced pressure. After cooling to room temperature, the mixture was placed under nitrogen and the polymer was dissolved in 61.8 g of n-butyl acetate. Then 25.0 g of isophorone diisocyanate (IPDI) were added and the mixture was heated to 50° C. Addition of 10 mg of zinc neodecanoate dissolved in 1 ml of n-butyl acetate started the reaction, which was conducted over the course of 4.5 h at 50° C. until an NCO content of 2.84%. Subsequently, the reaction was ended by cooling to −20° C. The reaction product A.14b was used directly in stage 2 without further workup.

Stage 2 (A.14):

7.0 g of the hydrophobic hyperbranched polyester core A.14a were dissolved in 7.0 g of n-butyl acetate in a 500 ml three-neck flask equipped with a reflux condenser and an internal thermometer, and admixed under nitrogen with 12.1 g of the reaction mixture A.14b. Then the mixture was heated to 80° C. and the reaction was started by adding 2 mg of DBTL dissolved in 1 ml of n-butyl acetate. After the complete conversion of all NCO groups (NCO content 0%), the mixture was cooled and the solvent was removed under reduced pressure. Finally, the linear dendritic copolymer A.14 (Mn=2200 g/mol) was obtained in the form of a yellow liquid of high viscosity, which was completely water-soluble.

Comparative Example 15: Hyperbranched Polyester A.15 (Noninventive)

In a four-neck flask provided with stirrer, internal thermometer, nitrogen inlet tube and descending condenser with a collecting vessel, an initial charge of 92.1 g of the trifunctional alcohol glycerol and 142.0 g of succinic acid sparged with dry nitrogen was admixed with 0.1 g of DBTL catalyst, and the reaction mixture was heated to 160-180° C. while stirring. After a reaction time of 2.5 h, in which 30 ml of water separated out (conversion 68%), the mixture was cooled to 140° C. and a further 50.6 g of the trifunctional alcohol glycerol were added to the reaction mixture. Subsequently, it was heated to 190° C. while stirring. After a reaction time of a further 4 h, a vacuum of 400 mbar was applied for the period of 1 h. Then the reaction was ended by cooling to room temperature. The polymer A.15 (Mn=660 g/mol; Mw=2050 g/mol; OH number: 536 mg KOH/g polymer; acid number: 24 mg KOH/g polymer) was obtained in the form of a yellow liquid of high viscosity, which, after neutralization of 50% of the terminal carboxylic acid groups with triethanolamine, had very good water solubility. The polymer A.15 was used in this partly neutralized form for the further experiments.

Comparative Example 16: Hyperbranched Polyester A.16 (Noninventive)

A four-neck flask provided with stirrer, internal thermometer, nitrogen inlet tube and descending condenser with a collecting vessel was initially charged with 152.1 g of trimethylolpropane and 348.9 g of adipic acid, which were sparged with dry nitrogen, and the reaction mixture was heated to 160-170° C. while stirring. After a reaction time of 70 min, in which 44 ml of water were separated out (conversion 51%), the reaction was ended by cooling to room temperature. The polymer A.16 (Mn=710 g/mol; Mw=75 160 g/mol; OH number: n.d.; acid number: 134 mg KOH/g polymer) was obtained in the form of a yellow liquid of high viscosity, which, after neutralization of 100% of the terminal carboxylic acid groups with triethanolamine, had very good water solubility. The polymer A.16 was used in this completely neutralized form for the further experiments.

Example 17: Preparation and Redispersion of a Solid Formulation ("Solid Solution")

In a beaker, the appropriate hyperbranched polyester was dissolved in isopropanol and then the solution was admixed with the fungicide pyraclostrobin. The total concentration of the homogeneous polymer/active ingredient mixture in isopropanol thus prepared was 20% by weight, and a polymer/active ingredient ratio of 3:1 was always established. The solution was then poured out onto small aluminum sheets, such that, after the removal of the organic solvent under reduced pressure (<100 mbar, 50° C., 24 h), it was possible to obtain thin films (<1 mm). With the aid of small amounts of dried film material, it was attempted to produce 1% by weight solutions by redispersion in distilled water. If successful, the polymer/active ingredient dispersion in water was assessed with regard to its quality (turbity, formation of sediment). The data for the solid formulations produced are compiled in table 1.

TABLE 1

| Hyperbranched polyester | Visual assessment of the film after production | Visual assessment after redispersion |
|---|---|---|
| A.1 | clear | clear |
| A.9 | clear | clear |
| A.10 | clear | clear |

Example 18—Solubilization of Piroxicam, Carbamazepine, Estradiol and Clotrimazole 2 g of polymer were weighed into a 50 ml beaker. Subsequently, 0.2 g of active ingredient in each case was weighed into the mixture in order to obtain an oversaturated solution. Then sufficient pH 7.0 phosphate buffer was added that a polymer:phosphate buffer mass ratio of 1:9 was present. The mixture was then stirred at room temperature with the aid of a magnetic stirrer for 72 h. After a rest time of 1 h, excess (i.e. unsolubilized) active ingredient was removed by filtration. The clear or opaque solution thus obtained was subsequently analyzed for its active ingredient content by means of UV spectroscopy or HPLC. The wavelengths of the UV spectroscopy measurements (if usable) are compiled in table 2. The results of the solubilization tests are compiled in table 3.

TABLE 2

| Active ingredient | Wavelength of the UV measurement [nm] |
|---|---|
| Piroxicam | 356 |
| Carbamazepine | 286 |
| Estradiol | 282 |
| Clotrimazole | HPLC |

TABLE 3

Solubility of active ingredients [mg/l] in the presence of hyperbranched polyester

| Polyester | Piroxicam | Carbamazepine | Estradiol | Clotrimazole |
|---|---|---|---|---|
| none | 420 | 140 | <100 | <100 |
| A.1[a)] | 6200 | 1700 | 1100 | 4700 |
| A.6 | n.d.[b)] | 550 | 3350 | 1390 |
| A.9 | 1300 | 2700 | 300 | 5500 |
| A.10 | 4800 | 1800 | 900 | 5600 |

[a)]In this test, the degree of neutralization of the carboxylic acid groups was 100%.
[b)]n.d. = not determined Example 19—Solubilization of Pyrene, Pyraclostrobin and Fipronil 100 mg of polymer were weighed into a 50 ml beaker and dissolved in 9.900 g of distilled water. Subsequently, 100 mg of active ingredient in each case were weighed into the mixture in order to obtain an oversaturated solution. The mixture was then stirred with the aid of a magnetic stirrer at room temperature for 24 h. After a rest time of 1 hour, excess (i.e. unsolubilized) active ingredient was removed by centrifugation. The clear or opaque solution thus obtained was subsequently analyzed for its active ingredient content by means of UV spectroscopy. The wavelengths of the UV spectroscopy measurements are compiled in table 4. The results of the solubilization tests are compiled in table 5.

TABLE 4

| Active ingredient | Wavelength of the UV measurement [nm] |
|---|---|
| Pyrene | 334 |
| Pyraclostrobin | 277 |
| Fipronil | 280 |

TABLE 5

Solubility of active ingredients [mg/l] in the presence of hyperbranched polyester

| Polymer | Pyrene | Pyraclostrobin | Fipronil |
|---|---|---|---|
| none | 0.1 | 22.5 | 3 |
| A.1 | 234 | 619 | 104 |
| A.2 | 189 | 531 | n.d. |
| A.3 | 169 | n.d. | 144 |
| A.4 | 224 | 578 | 174 |
| A.5 | 81 | n.d. | 174 |
| A.6 | 103 | n.d. | 198 |
| A.7 | 247 | 558 | n.d. |
| A.8 | 227 | 630 | n.d. |
| A.9 | 248 | 579 | 141 |
| A.10 | 281 | 736 | 147 |
| A.11 | 200 | n.d. | 227 |
| A.12 | 180 | 554 | 290 |
| A.13 | 160 | n.d. | 109 |
| A.14 | 80 | n.d. | 74 | n.d. = not determined

Example 20—Comparative Tests of Solubilization with Noninventive Hyperbranched Polyesters The hyperbranched polyesters a.1 to a.5 and c.1 were prepared as described in WO 2007/125028 in examples I.1 to I.5 and II.2. In addition, the above-described hyperbranched polyesters a.15 and a.16 were tested. All polymers were tested for their solubilization by the method described above (see example 19). The results are compiled in table 6.

TABLE 6

Solubilization with noninventive hyperbranched polyesters

| Polymer | Starting materials | Pyrene | Fipronil |
|---|---|---|---|
| a.1 | Succinic acid + 12EO-TMP | 0.1 | n.d. |
| a.2 | Succinic acid + 5EO-glycerol | 0.1 | n.d. |
| a.3 | Adipic acid + 12EO-TMP | 0.3 | n.d. |
| a.4 | Adipic acid + 5EO-glycerol | 1.2 | n.d. |
| a.5 | Succinic acid + glycerol | 0.1 | n.d. |

TABLE 6-continued

Solubilization with noninventive hyperbranched polyesters

| Polymer | Starting materials | Pyrene | Fipronil |
|---------|--------------------|--------|----------|
| c.1 | Adipic acid + glycerol joined to MPEG750 | 14 | n.d. |
| A.15 | Succinic acid + glycerol | 2 | 11 |
| A.16 | Adipic acid + TMP | 45 | n.d. | n.d. = not determined.
TMP: trimethylolpropane;
12EO-TMP: TMP ethoxylated with 12 mol of EO per mole of TMP;
5EO-glycerol: glycerol ethoxylated with 5 mol of EO per mole of glycerol;
MPEG750: monomethyl polyethylene glycol, molar mass 750 g/mol.

The direct comparison of polymers (a.1)-(a.5) and A.15/A.16 (table 6) with the inventive polymers A.1-A.10 which are structurally similar but based on sebacic acid and/or ASA and/or PIBSA (table 5) shows that the inventive polymers have significantly higher solubilization capacities (by 1-3 orders of magnitude).

The direct comparison of the linear dendritic (PEG-functionalized, hyperbranched) polyester (c.1) (table 6) with the inventive linear dendritic polyesters A.11-A.14 which are structurally similar but based on sebacic acid and/or ASA and/or PIBSA (table 5) shows that the inventive polymers here too have significantly higher solubilization capacities (by approx. 2 orders of magnitude).

The invention claimed is:

1. A hyperbranched polyester comprising a hydrophobic dicarboxylic acid and a trifunctional alcohol, wherein
    the hydrophobic dicarboxylic acid is an aliphatic $C_{10}$-$C_{32}$ dicarboxylic acid, or a succinic acid unit having a $C_3$-$C_{40}$ group,
    wherein the trifunctional alcohol is trimethylolethane, trimethylolpropane, bis(trimethylolpropane), pentaerythritol, or an alkoxylated derivative of glycerol, trimethylolethane, trimethylolpropane, bis(trimethylolpropane), or pentaerythritol, and
    wherein the hyperbranched polyester is joined to a polyalkylene oxide group, and
    wherein the hyperbranched polyester is joined to the polyalkylene oxide group by a polyisocyanate linker.

2. The hyperbranched polyester of claim 1, wherein the functional $C_1$-$C_{24}$ end group of the hyperbranched polyester is a succinic acid derivative.

3. The hyperbranched polyester of claim 1, wherein the $C_{10}$-$C_{32}$ dicarboxylic acid is sebacic acid.

4. The hyperbranched polyester of claim 1, wherein the hydrophobic dicarboxylic acid is a succinic acid unit having a $C_3$-$C_{40}$ group.

* * * * *